(12) United States Patent
Betts et al.

(10) Patent No.: US 11,383,009 B2
(45) Date of Patent: *Jul. 12, 2022

(54) RAPAMYCIN 40-O-CYCLIC HYDROCARBON ESTERS, COMPOSITIONS AND METHODS

(71) Applicant: BIOTRONIK AG, Buelach (CH)

(72) Inventors: Ronald E. Betts, La Jolla, CA (US); John Dang Nguyen, San Diego, CA (US); Beatris Flores, San Diego, CA (US)

(73) Assignee: Biotronik AG, Buelach (CH)

( * ) Notice: Subject to any disclaimer, the term of this patent is extended or adjusted under 35 U.S.C. 154(b) by 8 days.

This patent is subject to a terminal disclaimer.

(21) Appl. No.: 16/933,821

(22) Filed: Jul. 20, 2020

(65) Prior Publication Data

US 2020/0345902 A1 Nov. 5, 2020

Related U.S. Application Data

(60) Division of application No. 16/359,187, filed on Mar. 20, 2019, now Pat. No. 10,751,450, which is a continuation-in-part of application No. 15/829,012, filed on Dec. 1, 2017, now abandoned, which is a division of application No. 15/212,987, filed on Jul. 18, 2016, now Pat. No. 9,867,911, which is a continuation of application No. 14/406,198, filed as application No. PCT/EP2013/061343 on Jun. 3, 2013, now Pat. No. 9,408,884.

(60) Provisional application No. 61/657,049, filed on Jun. 8, 2012.

(51) Int. Cl.

| | | |
|---|---|---|
| *A61L 31/16* | (2006.01) | |
| *A61L 31/10* | (2006.01) | |
| *C07D 498/18* | (2006.01) | |
| *C08L 67/04* | (2006.01) | |
| *A61K 47/46* | (2006.01) | |
| *A61K 47/26* | (2006.01) | |
| *A61K 38/17* | (2006.01) | |
| *A61K 38/16* | (2006.01) | |
| *A61K 36/68* | (2006.01) | |
| *A61K 31/685* | (2006.01) | |

(52) U.S. Cl.
CPC ............ *A61L 31/16* (2013.01); *A61K 31/685* (2013.01); *A61K 36/68* (2013.01); *A61K 38/168* (2013.01); *A61K 38/1709* (2013.01); *A61K 47/26* (2013.01); *A61K 47/46* (2013.01); *A61L 31/10* (2013.01); *C07D 498/18* (2013.01); *C08L 67/04* (2013.01); *A61L 2300/416* (2013.01); *A61L 2300/606* (2013.01); *A61L 2300/608* (2013.01)

(58) Field of Classification Search
CPC .............. C08L 67/04; A61L 2300/416; A61L 2300/606; A61L 2300/608; A61L 31/10; A61L 31/16; C07D 498/18; A61K 31/685; A61K 36/68; A61K 38/168; A61K 38/1709; A61K 47/26; A61K 47/46
See application file for complete search history.

(56) References Cited

U.S. PATENT DOCUMENTS 9,867,911 B2 * 1/2018 Betts ..................... C08L 67/04

\* cited by examiner

*Primary Examiner* — Erich A Leeser
(74) *Attorney, Agent, or Firm* — Lewis Kohn & Walker LLP; David M. Kohn (57) ABSTRACT

A new class of rapamycin 40-O-cyclic hydrocarbon esters is disclosed. The 40-O position of the rapamycin ester has the form 40-O—R, where R is C(O)—$(CH_2)_n$—X, n is 0, 1 or 2, and X is a cyclic hydrocarbon having 3-8 carbons, optionally containing one or more unsaturated bonds, and one or more linear $(CH_2)_n$ and/or cyclic (X) carbon atoms may have an OH or halide group. Also disclosed are therapeutic compositions and methods that employ the novel analogs.

3 Claims, 7 Drawing Sheets

RAPAMYCIN 40-O-CYCLIC HYDROCARBON ESTERS, COMPOSITIONS AND METHODS

RELATED APPLICATIONS

This application is a divisional of U.S. application Ser. No. 16/359,187 filed Mar. 3, 2019, which is a continuation-in-part of U.S. application Ser. No. 15/829,012, which is a divisional application of U.S. application Ser. No. 15/212,987, filed Jul. 18, 2016, now U.S. Pat. No. 9,867,911, which is a continuation application of U.S. application Ser. No. 14/406,198, filed Dec. 5, 2014, now U.S. Pat. No. 9,408,884, which is a § 371 application of International Application Serial No. PCT/EP2013/061343 filed Jun. 3, 2013, which claims the benefit of priority from U.S. Provisional Application Ser. No. 61/657,049, filed Jun. 8, 2012.

The present invention relates to a rapamycin 40-O-cyclic hydrocarbon ester, compositions containing the ester, and methods of use of the compound and composition.

Rapamycin is a macrocyclic triene compound that was initially extracted from a streptomycete (*Streptomyces hygroscopicus*) isolated from a soil sample from Easter Island (Vezina et al., J. Antibiot. 28:721 (1975); U.S. Pat. Nos. 3,929,992; 3,993,749).

A variety of rapamycin derivatives designed to improve its solubility, stability, and/or pharmacological profile have been reported. See, for example, Adamczyk et al. Lipase Mediated Hydrolysis of Rapamycin 42-Hemisuccinate Benzyl and Methyl Esters, Tetrahedron Letters, Vol. 35, No. 7, pp. 1019-1022, 1994, and U.S. Pat. Nos. 5,258,389, 5,665,772, and 6,440,990.

One of the major therapeutic uses of rapamycin and its derivatives has been for the treatment of restenosis. Restenosis after percutaneous transluminal coronary angioplasty (PTCA) remains a major limitation (Hamon, M. et al., Drug Therapy, 4:291 301 (1998)). In a typical PTCA procedure, the region of vascular blockage is expanded by balloon angioplasty and a stent is expanded against the vessel walls to maintain the vessel in an expanded diameter state. With a bare metal stent restenosis of the vessel may occur within 3-6 months or more in more than 30% of the cases, requiring additional intervention to restore the vessel to an expanded diameter. Restenosis after PTCA is thought to be a two-component process of both intimal hyperplasia and vascular remodeling, the former coming initially, the latter occurring later in the process (Hoffman, R. et al., Circulation, 94:1247 1254 (1996); Oesterle, S. et al., Am. Heart J., 136:578 599 (1998)).

To reduce the rate of restenosis in a PTCA procedure, the stent may be coated with rapamycin or a rapamycin derivative in a form that allows slow release of the drug from the stent against the endothelial cells of the vessel, typically over a two-week to several-month interval. The stent coating may consist of a polymer, e.g., bioerodable polymer, with encapsulated drug, or the drug itself may form a cohesive coating. In either case, the coating may be susceptible to cracking as the stent is expanded at the implantation site, and any loose pieces of coating that break off can be a significant clotting hazard in the bloodstream. Another problem that has been observed heretofore in rapamycin stents is relatively poor drug stability, as evidence by mass balance measurement on the amounts of active drug released from the stent coatings, typically showing less than 40% of active drug recovered after elution from the stent.

In one aspect, the invention includes a rapamycin 40-O-cyclic hydrocarbon ester having the structure:

where R is $C(O)-(CH_2)_n-X$, n is 0, 1 or 2, X is a cyclic hydrocarbon having 3-8 carbons, optionally containing one or more unsaturated bonds, one or more linear-chain or cyclic carbon atoms may contain an OH or halide substitution, and the rapamycin parent structure may contain substitutions at other positions.

Exemplary R groups include:

In another aspect, the invention includes a method of treating any of the following conditions in a mammal: (i) restenosis; (ii) wound healing; (iii) vascular injury; (iv) vascular inflammation; (v) transplantation rejection; (vi) proliferative ophthalmic diseases, including wet age-related macular degeneration (AMD) and diabetic macular edema (DME); (vii) uveitis; (viii) cancer; (ix) various skin conditions such asatopic dermatitis, eczema, tuberous sclerosis, neurofibromatosis, lichen planus and the like; (x) ear-nose-throat treatments such as sinusitis treatment with sinus stents or balloons by administering to the mammal, a therapeutic amount of the rapamycin 40-O-cyclic hydrocarbon ester. For inhibiting restenosis at a vascular injury site, the rapamycin ester may be administered from a drug-eluting stent placed at the vascular injury site.

With respect to treating uveitis in a mammal, it is known in the art that uveitis is a form of eye inflammation that affects the uvea, which is the middle fibrous protective layer of tissue in the eye wall. Possible causes of uveitis are infection, acute injury, or autoimmune disorder. Due to the specific location of the uvea, treatment regimens have been notorious difficult and, if uveitis is left untreated, the disease can progress to partial vision loss and even total blindness. In one aspect, the present invention provides for a method of treating uveitis in a mammal, comprising applying an effective amount of the rapamycin 40-O-cyclic hydrocarbon ester of the present invention directly to an eye of the mammal.

With respect to treating wet age-related macular degeneration in a mammal, it is well-known that AMD is a progressive eye condition that is considered the most common cause of blindness in developed countries. AMD causes damage to the retina, with the most prevalent form of the disease occurring when blood vessel growth is hyperstimulated by the protein vascular endothelial growth factor (VEGF). While there are known antibody treatments (anti-VEGF) available, such formulations require frequent dosing and may cause some reversion to a more recalcitrant form of AMD. In one aspect, the present invention provides a method of treating AMD in a mammal, the method comprising applying an effective amount of the rapamycin 40-O-cyclic hydrocarbon ester of the present invention directly to an eye of the mammal.

Also disclosed is a drug-eluting stent having an expandable stent body formed of one or more filaments and carried on the one or more filaments, a coating containing the above rapamycin 40-O-cyclic hydrocarbon ester. The coating may be formed of the rapamycin compound alone, or formed of a polymer, e.g., bioerodable polymer such as polylactic acid, containing the rapamycin ester in entrapped form. Other suitable polymers include poly(caprolactone), poly(trimethylene carbonate), polyester amide, poly(glycolide), polyhydroxyalkanoates including poly(hydroxyvalerate), poly(hydroxybutyrate), poly(hydroxybutyrate-co-valerate), polyorthoester, polyanhydride, poly(glycolic acid). The stent is used in a method for inhibiting restenosis at the site of vascular injury, by placing the stent at the site of vascular injury.

One specific aspect of the invention is directed to a method of treating proliferative ophthalmic diseases, including wet age-related macular degeneration (AMD) and diabetic macular edema (DME), and uveitis by administering to the mammal, a therapeutic amount of the rapamycin 40-O-cyclic hydrocarbon ester by way of an intravitreal injection of a formulation comprising or consisting of ethanol and the rapamycin 40-O-cyclic hydrocarbon ester.

Further disclosed are pharmaceutical compositions, including microparticle compositions, such as liposomes and bioerodable polymer particle compositions, containing the rapamycin ester in an encapsulated or captured form for release over time from a site of administration or implantation of the composition. Microparticles containing the rapamycin analog may be inherently porous with pore sizes ranging from about 5 nanometers to about 10 microns in diameter.

In still another embodiment, the invention includes an improvement in an intravascular stent of the type having an expandable stent body formed of one or more filaments, such as a metal-filament stent, and carried on the one or more filaments, a polymer coating containing 40%-80% polymer, such as a bioerodable polymer, and 20% to 60% rapamycin compound having a 40-position —OH or —O(CH)$_n$OH substituent, where n=1 to 5. The improvement, which significantly reduces the tendency of the coating to flake or crack when the stent body is expanded, includes substituting in the rapamycin compound, the rapamycin 40-O-cyclic hydrocarbon ester of the invention.

These and other objects and features of the invention will become more fully apparent when the following detailed description of the invention is read in conjunction with the accompanying figures.

I. DEFINITIONS

"Rapamycin" refers to the macrocyclic triene compound having the structure shown below, where the 40 position is the ring carbon position shown below to which an OR group is attached, where R is H for rapamycin. Although not shown, the term "rapamycin" is also intended to encompass rapamycin analogs having substitutions at positions other than the 40-position, such as the non-position-40 substitutions and modifications shown in U.S. Pat. Nos. 4,316,885, 4,650,803, 5,102,876, 5,138,051, 5,118,678, 5,118,677, 5,100,883, 5,151,413, 5,120,842, 5,120,725, 5,120,727, and 5,310,903, 5,665,772, and 6,440,990.

A "rapamycin 40-O-cyclic hydrocarbon ester" refers to a rapamycin analog having a 40-position —OR, where R is C(O)—(CH$_2$)$_n$—X, n is 0, 1 or 2, X is a cyclic hydrocarbon having 3-8 carbons, optionally one or more unsaturated bonds, and one or more linear (CH$_2$)$_n$ and/or cyclic (X) carbon atoms may have an OH or halide group. Optionally, the rapamycin parent structure may include substitutions at positions other than the 40-O position, such as described above.

II. SYNTHESIS OF RAPAMYCIN 40-O-CYCLIC HYDROCARBON ESTERS

Table I below shows the R group for a number of exemplary analogs formed in accordance with the present invention.

TABLE 1

As detailed below, compounds 1-4 and 7 can be prepared by reacting rapamycin with the carbonyl chloride of the ester R group to be added, where the carbonyl chloride is readily prepared by known methods or obtained commercially. Compounds 5 and 6, in which R has one or more OH substituents, can be more easily prepared by reacting rapamycin with the free acid of the desired R group in the presence of carbodiimide, thus avoiding the somewhat complicated chemistry of forming a carbonyl chloride in the presence of a free OH group. It will be appreciated from these synthetic schemes how other R groups, e.g., where R is a seven- or eight-member cyclic ring, with or without OH or halide substituents, can be prepared.

IIA. Rapamycin 40-O-Cyclic Hydrocarbon Ester with Cyclopropanecarbonyl Chloride (Compound 1)

Compound 1 was prepared by dissolving 200 mg rapamycin in 1.0 mL methylene chloride contained in a 3.8-mL borosilicate glass vial with stirring bar and capped. With stirring, 30 μL pyridine was added followed with 100 μL cyclopropanecarbonyl chloride, as received. The reaction vessel was placed at ambient temperature and reaction continued with stirring for 1 hour. The reaction mixture was transferred into a 125-mL separatory funnel with a Pasteur pipette. 50 mL of ethyl acetate was added to the reaction solution and the resulting solution washed with 6 mL 1N HCl combined with 30 mL DI water. The organic phase was collected into a beaker and the remaining aqueous layer was back-extracted with 20 mL ethyl acetate. The acid washed organic phases were combined and further washed with 50 mL NaCl brine until a pH of 7 was reached by litmus paper. The solution was then dried using anhydrous sodium sulfate and concentrated under vacuum to result in a light yellow oil.

The product was purified using a CombiFlash system via normal phase chromatography. RediSep Rf 24 g Gold silica column was used with a hexanes/ethyl acetate solvent system. Purification started at 80/20 hexanes/ethyl acetate for the first 20 minutes and ramped up to a 50/50 hexanes/ethyl acetate mobile phase over a period of 27 minutes. As determined by HPLC analyses, fractions containing the ester product were combined and concentrated under vacuum to yield approximately 50% of the theoretical. The purified product was reconstituted in 280 µL methanol and precipitated into 2.6 mL cold DI water. The white solid was filtered and dried in a vacuum oven held at 45° C. and under a pressure of −28.0 in Hg for 24 hours.

The product was analyzed by High Resolution LCMS. Table II compares the exact mass calculated and exact mass found for the title compound ($C_{55}H_{83}NO_{14}$) with $Na^+$ adduct. Also shown is dried product recovery.

TABLE II

| $C_{55}H_{83}NO_{14}Na$ | |
|---|---|
| Exact Mass Calculated | 1004.5711 |
| Exact Mass Found | 1004.5696 |
| Recovery | |
| Sirolimus Starting Material | 200 mg |
| Amount of Product Recovered | 80 mg |

IIB. Rapamycin 40-O-Cyclic Hydrocarbon Ester with Cyclobutanecarbonyl Chloride (Compound 2)

Compound 2 was prepared by the same scheme for Compound 1, but substituting 100 µL cyclobutanecarbonyl chloride, as received, for 100 µL cyclopropanechloride. The compound was purified as described for Compound 1 and analyzed by High Resolution LCMS.

Table III compares the exact mass calculated and exact mass found for the title compound ($C_{56}H_{85}NO_{14}$) with $Na^+$ adduct. Also shown is dried product recovery.

TABLE III

| $C_{56}H_{85}NO_{14}Na$ | |
|---|---|
| Exact Mass Calculated | 1018.5868 |
| Exact Mass Found | 1018.5791 |
| Recovery | |
| Sirolimus Starting Material | 200 mg |
| Amount of Product Recovered | 73 mg |

IIC. Rapamycin 40-O-Cyclic Hydrocarbon Ester with Cyclopentanecarbonyl Chloride (Compound 3)

Compound 3 was prepared by the same scheme for Compound 1, but substituting 100 µL cyclopentane chloride, as received, for 100 µL cyclopropanecarbonyl chloride. The compound was purified as described for Compound 1 and analyzed by High Resolution LCMS.

Table IV compares the exact mass calculated and exact mass found for the title compound ($C_{57}H_{87}NO_{14}$) with $Na^+$ adduct. Also shown is dried product recovery.

TABLE IV

| $C_{57}H_{87}NO_{14}Na$ | |
|---|---|
| Exact Mass Calculated | 1032.6024 |
| Exact Mass Found | 1032.5951 |
| Recovery | |
| Sirolimus Starting Material | 200 mg |
| Amount of Product Recovered | 84 mg |

IID. Rapamycin 40-O-Cyclic Hydrocarbon Ester with Cyclohexanecarbonyl Chloride (Compound 4)

Compound 4 was prepared by the same scheme for Compound 1, but substituting 100 µL cyclohexanecarbonyl chloride, as received, for 100 µL cyclopropanecarbonyl chloride. The compound was purified as described for Compound 1 and analyzed by High Resolution LCMS.

Table V compares the exact mass calculated and exact mass found for the title compound ($C_{58}H_{89}NO_{14}$) with $Na^+$ adduct. Also shown is dried product recovery.

TABLE V

| $C_{58}H_{89}NO_{14}Na$ | |
|---|---|
| Exact Mass Calculated | 1046.6181 |
| Exact Mass Found | 1046.6123 |
| Recovery | |
| Sirolimus Starting Material | 200 mg |
| Amount of Product Recovered | 122 mg |

IIE. Rapamycin 40-O-Cyclic Hydrocarbon Ester with 4-Hydroxycyclohexane Carboxylic Acid (Compound 5)

Compound 5 was prepared by dissolving 94 mg rapamycin in 2.5 mL methylene chloride in a 7.5-mL borosilicate glass vial with a stir bar and capped. The solution was stirred at ambient temperature for two minutes, then 78.0 mg 4-N,N-dimethylaminopyridine was added and allowed to dissolve. 118 mg racemic 4-hydroxycylohexane carboxyl acid and 204 mg N,N-dicyclohexylcarbodiimide were added in the reaction mixture. The reaction continued stirring at ambient temperature for 2 hours. Synthesis of product was verified by taking 2 µL of the reaction mixture and diluting in 0.5 mL acetonitrile and analyzed by High Resolution LCMS. Table VI compares the exact mass calculated and exact mass found for the title compound ($C_{58}H_{89}NO_{15}$) with $Na^+$ adduct.

TABLE VI

| $C_{58}H_{89}NO_{15}Na$ | |
|---|---|
| Exact Mass Calculated | 1062.6130 |
| Exact Mass Found | 1062.6130 |

IIF. Rapamycin 40-O-Cyclic Hydrocarbon Ester with Shikimic Acid (Compound 6)

Compound 6 was prepared by dissolving 14.0 mg rapamycin in 100 µL methylene chloride contained in a 1.5-mL HPLC glass vial with stirring bar and capped. The solution was stirred at ambient temperature for two minutes, then 1.0 mg 4-N,N-dimethylaminopyridine was added. In a second 1.5-mL HPLC glass vial, 2.0 mg shikimic acid and 100 µL dimethylformamide were combined and mixed. Using a syringe, the shikimic acid/dimethylformamide solution mixture was added dropwise into the rapamycin solution. 3.0 mg N,N-dicyclohexylcarbodiimide was added and the reaction was continued with stirring for 19 hours at ambient temperature. Synthesis of product was verified by taking 2 µL of the reaction mixture and diluting in 0.5 mL acetonitrile and analyzed by High Resolution LCMS. Table VII compares the exact mass calculated and exact mass found for the title compound ($C_{58}H_{87}NO_{17}$) with $Na^+$ adduct.

TABLE VII

| $C_{58}H_{87}NO_{17}Na$ | |
|---|---|
| Exact Mass Calculated | 1092.5872 |
| Exact Mass Found | 1092.5850 |

IIG. Rapamycin 40-O-Cyclic Hydrocarbon Ester with Cyclohexaneacetyl Chloride (Compound 7)

Compound 7 was prepared by dissolving 20 mg rapamycin in 100 µL methylene chloride contained in a 1.5-mL HPLC glass vial with stirring bar and capped. With stirring, 3 µL pyridine was added and followed with 104 cyclohexaneacetyl chloride, as received. The reaction vessel was placed at ambient temperature and reaction continued with stirring for 1 hour.

The product was analyzed by High Resolution LCMS. Table VIII compares the exact mass calculated and exact mass found for the title compound ($C_{59}H_{91}NO_{14}$) with $Na^+$ adduct.

TABLE VIII

| $C_{59}H_{91}NO_{14}Na$ | |
|---|---|
| Exact Mass Calculated | 1060.6337 |
| Exact Mass Found | 1060.6337 |

III. COMPOUND PROPERTIES

IIIA. Increased Ductility of a Coating Formed from the Analog

The 40-O-cyclic hydrocarbon rapamycin esters of the invention are designed for use in a variety of therapeutic uses, as detailed in Section IV below. One of the important uses is for slow-release of the drug from a stent coating in treating/preventing restenosis following percutaneous transluminal coronary angioplasty (PTCA). In this procedure, the coated stent is delivered to the site of vascular injury in a contracted, low-diameter condition in a balloon catheter, and then expanded to the dimensions of the treated vessel at the site. In this application, it is important that the drug coating is sufficiently ductile that it does not crack or flake off the outer stent surface during stent expansion, since loose pieces of coating, if released into the bloodstream, may present a serious clotting hazard.

Figure 1:
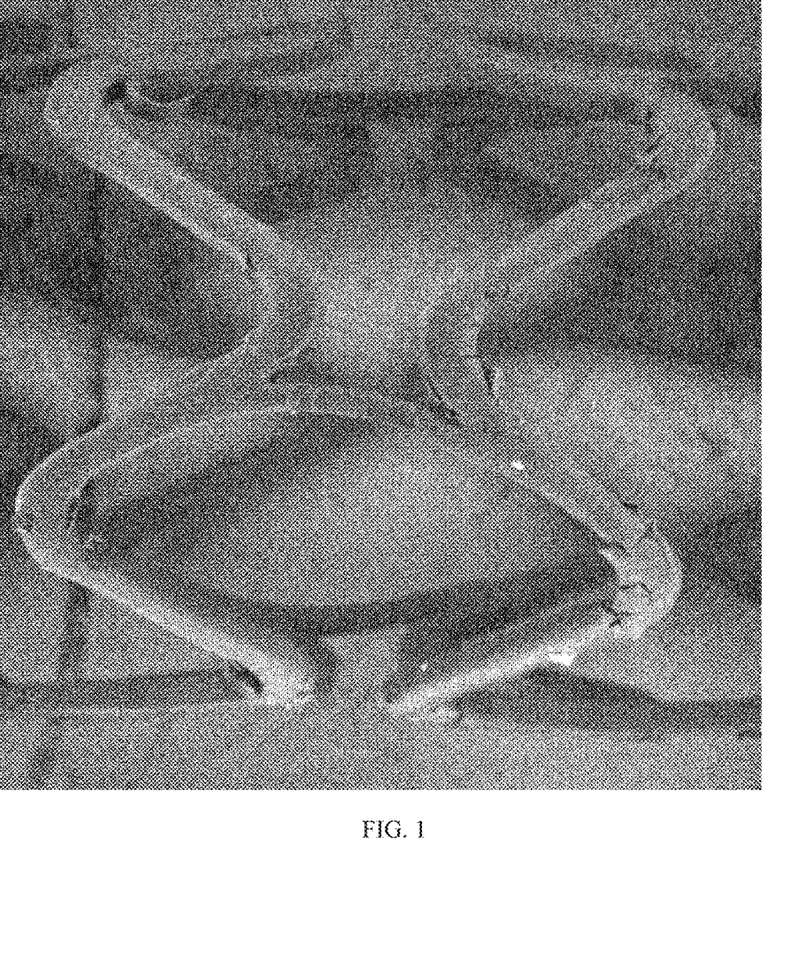
FIG. 1 shows the effects of stent expansion on a polymer coating containing 50 weight percent rapamycin on the stent filaments.
Figure 2:
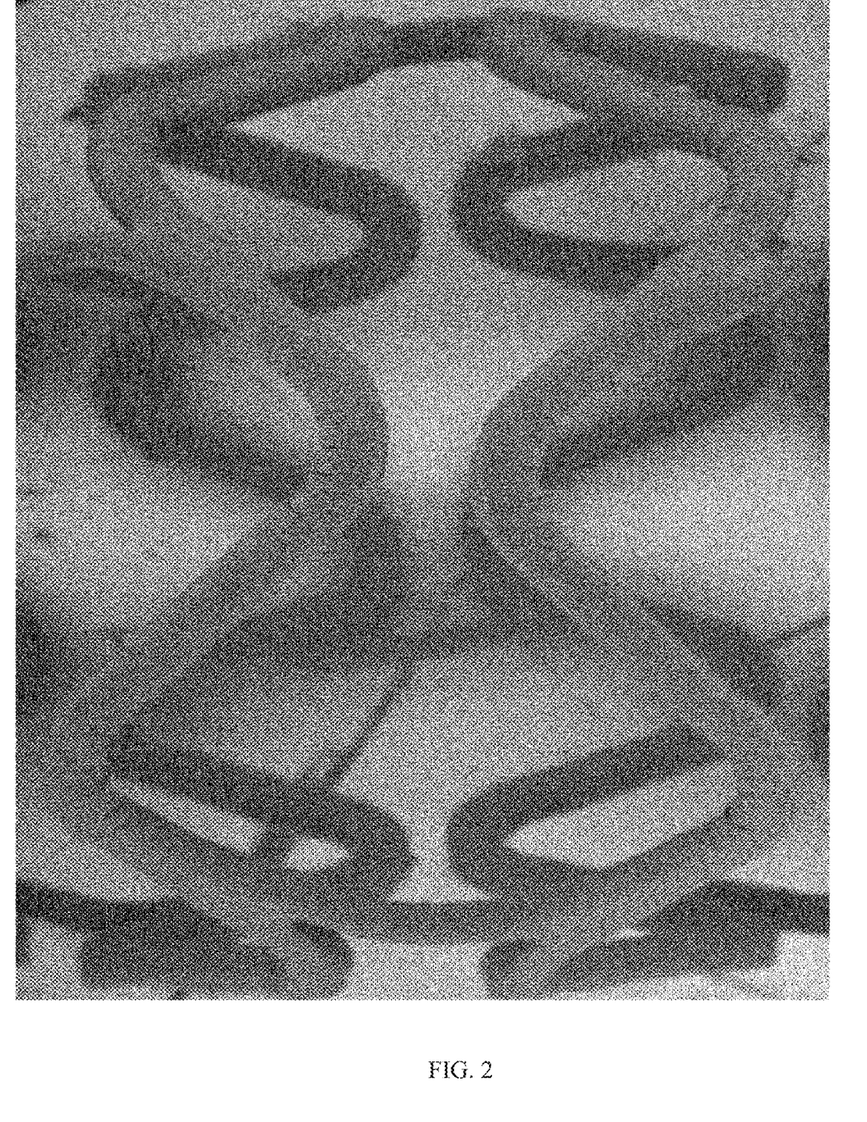
FIG. 2 shows the effects of stent expansion on a polymer coating containing 50 weight percent rapamycin 40-O-cyclic hydrocarbon ester in accordance with one aspect of the invention.

In accordance with one of the unexpected advantages of the present invention, it has been discovered that a coating formed with the compounds of the present invention is substantially more ductile, i.e., less prone to cracking, than a coating formed with rapamycin. This property can be seen from the photomicrographs of FIGS. 1 and 2, which show the condition of a stent coating after stent expansion in a stent formed of a 1:1 weight ratio of a 40-O-cyclic hydrocarbon rapamycin ester and polylactic acid (FIG. 1) and a coating formed of a 1:1 weight ratio of Compound 1 (Table I) and polylactic acid (FIG. 2). As seen, the drug compound of the present invention provides for a coating that is more ductile, and more resistant to delamination and particle shedding and in general, appears to function as a plasticizer for the polylactate coating. An important advantage of the drug compound in this setting is that a coating with a high drug:polymer ratio can be prepared without the need for addition of a separate plasticizer, which may cause toxic responses, affect drug elution rates, and extend development times and increase production costs.

In one aspect, the invention includes an improvement in an intravascular stent of the type having an expandable stent body formed of one or more filaments, such as a metal-filament stent, and carried thereon, a drug-eluting polymer coating containing 40-80 weight percent polymer and 20 to 60 weight percent of a rapamycin compound having a 40-O—H or 40-O-linear alcohol group. The improvement, which significantly reduces the tendency of the coating to flake or crack when the stent body is expanded, includes substituting for the rapamycin compound, the rapamycin 40-O-cyclic hydrocarbon ester of the present invention.

IIIB. Drug Elution and Stability

This section examines the stability of the compounds of the invention when released from a reservoir over a several-day to several-week period. In one study, a series of stents were prepared with a suitable coating of drug/polymer mixture. The stents were fabricated from laser cut and electropolished 316L Stainless Steel and measured 16 millimeters in length. The coating mixture contained an equal weight of polylactic acid and each of the compounds to be evaluated. The mixture components were weighed, combined in a glass vial with acetone at room temperature and then vortexed until all of the materials dissolved. Each individual stent was weighed using a Mettler model XP105 balance. A Hamilton brand micro syringe with a capacity of 25 microliters and a 26 gauge dispensing needle was used to aspirate a column of the coating fluid from the glass vial. Each stent was held on a coating mandrel located under a stereo zoom microscope at 60× magnification.

The coating was applied to the outer surface of each of the stents by means of mounting the syringe into a KD Scientific model 100 syringe pump and then gradually metering the solution onto the stent struts in a uniform manner. After coating each of the stents was vacuum dried at room temperature under vacuum (25 inches Hg) for a period of 72 hours. The weight of the drug coating was confirmed by re-measurement of each stent and subtraction of the weight of the bare stent from the coated stent. The target weight of the coating was 500 micrograms which yielded a drug dose of 250 micrograms for each of the coated stents. Each stent was also visually inspected to confirm the integrity of the coating.

After visual inspection the stents were mounted onto 3.0 mm×16 mm angioplasty balloons using a hand crimper. The coated stents were subsequently deployed to a nominal diameter of 3.0 mm using a Braun Co. indeflator device filled with deionized water. The appropriate pressure for inflation was determined using the inflation table applicable to the angioplasty catheter. Upon balloon deflation, the stent was carefully removed and placed into a glass vial which was capped and saved for the elution analysis.

For elution comparison each stent was transferred into its respective 7-mL borosilicate vial and 4.0 mL 25% ethanol in water (w/w) elution medium was added. Each vial was capped and incubated statically in a 37° C. water bath. At specific time points, the elution medium was removed from each vial for analysis and replenished with 4.0 mL fresh elution medium. The amount of drug eluted during each time interval was determined by HPLC. After a cumulative incubation of 168 hours, the remaining drug in each stent was determined by exhaustive extraction by adding 4.0 mL acetonitrile to each stent for 20 minutes at ambient temperature followed by vortexing for 10 seconds. These conditions dissolve all drug and polymer remaining on the stent. Measurement of drug content from each exhaustive extraction was determined by direct analysis of the acetonitrile using HPLC as above. The amount of drug recovered at each time point and the exhaustive extraction was summed for each stent to determine the total amount of drug recovered, and the results for rapamycin and a rapamycin 40-O-cyclic hydrocarbon ester are shown in Table IX below.

TABLE IX

|  | Stent # | Drug Amount (µg) | Total Drug (µg) Recovered | % Recovery |
|---|---|---|---|---|
| Rapamycin | 1 | 238 | 84.6 | 35.6 |
|  | 2 | 238 | 103.4 | 43.4 |
|  | 3 | 236 | 125.2 | 53.1 |
|  | 4 | 236 | 71.6 | 32.8 |
|  | 5 | 241 | 109.1 | 45.3 |
| Average |  |  |  | 42.0 |
| Standard Deviation |  |  |  | 8.1 |
| Rapamycin | 6 | 228 | 192.5 | 84.6 |
| 40-Cyclic | 7 | 233 | 202.2 | 87.0 |
| Hydrocarbon | 8 | 233 | 198.7 | 85.3 |
| Ester | 9 | 236 | 202.4 | 85.8 |
|  | 10 | 241 | 197.8 | 82.2 |
| Average |  |  |  | 85.0 |
| Standard Deviation |  |  |  | 1.8 |

Average % recovery for rapamycin and the rapamycin 40-cyclic hydrocarbon ester were 42.0±8.1 and 85.0±1.8, respectively. This indicates that, unexpectedly, drug compounds of the present invention are more stable than rapamycin during elution conditions. This property is important as it allows for a lower drug dose to be utilized for patient treatment and also is beneficial for the drug product regulatory approval and quality control purposes because a high in vitro elution recovery is taken as evidence that the drug substance is stable, the test procedure is an accurate monitor of manufacturing quality and good drug product performance can be maintained.

IIIC. Inhibition of Restenosis

Trial A

Stainless steel coronary artery stents coated with the rapamycin 40-O-cyclic hydrocarbon ester of the invention were compared for their ability to control induced restenosis using a 28 day porcine arterial over stretch model. Four different groups of stents were evaluated with the drug compound and in different coating configurations. Group 1 consisted of five stainless steel stents which were first coated with a base layer consisting of a copolymer of polycaprolactone and poly L lactic acid. A topcoat of poly d,l lactic acid and 225 micrograms of rapamycin 40-O-cyclic hydrocarbon ester was then applied. Group 2 consisted of five stainless steel stents with the same base coat and a topcoat of poly d,l lactic acid and 100 micrograms rapamycin 40-O-cyclic hydrocarbon ester. Group 3 consisted of five stents with a drug topcoat consisting only of 100 micrograms of rapamycin 40-O-cyclic hydrocarbon ester applied directly to a base coat of the polycaprolactone-poly L lactic acid copolymer. Finally, Group 4 consisted of five stents with a base coat of parylene polymer and a topcoat of poly d,l lactic acid and 225 micrograms of rapamycin 40-O-cyclic hydrocarbon ester. All of the stents were 16 millimeters in length and were mounted on standard balloon delivery systems and were then sterilized with ethylene oxide gas. The balloon to artery ratio of the deployed stents was approximately 1.20:1.00. The matrix of coating layers and drug dosages was chosen with the intent to optimize the adhesion of the active drug compound to the stent surface and to determine the best means to transfer the drug to the surrounding vessel wall upon stent deployment.

The primary objective of this study was to evaluate the drug compound coating on stents to treat vessels in which injury was intentionally induced. Coronary artery measurements were made from angiographic images before stent deployment, immediately after deployment, and twenty-eight days after deployment to determine the effectiveness of the coated stent in reducing restenosis. Determination of angiographic late loss was made by subtraction of the minimum vessel lumen diameter of the stented vessel at 28 days post-implant from the minimal vessel lumen diameter at the time of implant. Determination of percent diameter stenosis was made at 28 days post-implant by the calculation of 100(1-MLD/refdia.) where MLD represents the minimum vessel lumen diameter at 28 days post-implant and refdia. is the average diameter of the vessel sections adjacent to the stented vessel. In prior porcine studies, vessels with implanted uncoated stainless steel stents indicated mean angiographic late loss values of one millimeter or more and mean angiographic percent diameter stenosis values of approximately 23%. Among the drug coated stents the Group 1 mean late loss value was 0.53 millimeters and the mean diameter stenosis was 11%. The Group 2 mean late loss value was 0.42 millimeters and the mean diameter stenosis was 11%. The Group 3 mean late loss value was 0.49 millimeters and the mean diameter stenosis was 12%. The Group 4 mean late loss value was 0.28 millimeters and the mean diameter stenosis was 10%. The significant reduction in both angiographic late loss and diameter stenosis values for all four of the drug coated groups with respect to expected values for the uncoated stents indicates a reduction in vessel restenosis due to the effect of the drug.

Trial B

Another set of in-vivo evaluations was designed to compare the effects of two different drugs coated onto magnesium stents. The devices were implanted in porcine coronary arteries using a balloon to artery ratio of 1.15:1.00. These magnesium stents were first coated with parylene C, a permanent, durable, elastic polymer. The stents were then coated with a specific coating matrix comprised of a drug and a polymer. By first applying the parylene coating the magnesium features of the stent are assumed to be protected from corrosion for periods of time which exceed the time required to deliver drug from the drug and polymer matrix. Group 1 of stents was coated with a matrix comprised of the drug rapamycin and polylactic acid such that the total dosage of the drug was 223 μg. Group 2 and Group 3 of stents were coated with a matrix of polylactic acid and the drug rapamycin 40-O-cyclic hydrocarbon ester such that the total dosage of that drug was 160 μg. All of the stents were mounted onto balloon delivery catheters which were then packaged and sterilized with ethylene oxide gas. Stents in each of the three separate groups were deployed into one of three porcine coronary arteries to a diameter of approximately 3.0 mm. Determination of the angiographic late loss and the percent diameter stenosis for each implanted vessel was made at 28 days post-implant. The results are listed in Table X below.

TABLE X

| Drug | Drug Weight Amount (μg) | Drug Molar Amount (pM) | Angiographic Late Loss (mm) | Diameter Stenosis (%) |
|---|---|---|---|---|
| Rapamycin-Group 1 (n = 5)* | 223 | 240 | 0.42 | 13.1 |
| 40-O-cyclic hydrocarbon ester-Group 2 (n = 2)* | 160 | 150 | 0.17 | 11.4 |
| 40-O-cyclic hydrocarbon ester-Group 3 (n = 5)* | 160 | 150 | 0.24 | 11.9 |

*n = number of stents

Although the drug dosage of the rapamycin 40-O-cyclic hydrocarbon ester groups 2 and 3 was almost 30% lower by weight and 37.5% lower in molar concentration than the drug dosage of the rapamycin group 1 there were significant reductions in both angiographic late loss and diameter stenosis values for both of the rapamycin 40-O-cyclic hydrocarbon ester groups compared to those values for the rapamycin group. This data demonstrates that with a lower dose the drug rapamycin 40-O-cyclic hydrocarbon ester is more effective in treatment of vascular restenosis than rapamycin.

IV. COMPOSITIONS AND APPLICATIONS

IVA. Compositions

In another aspect, the invention includes a composition incorporating the rapamycin 40-O-cyclic hydrocarbon rapamycin ester of the invention, where the composition serves a drug reservoir for release, typically in a controlled fashion, of the compound into a treatment site.

Micro and Macro Particles

One exemplary composition includes a suspension of polymer particles that can be introduced into a suitable treatment site in vivo via injection or delivery through a catheter. The polymer particles can be microporous, macroporous, or non-porous and can be formed of a polymer that acts as a suitable drug reservoir. Exemplary polymer particles are described, for example, in U.S. Pat. No. 5,135,740, incorporated by reference herein. Liposomal particles that incorporate the compound in encapsulated or membrane-entrapped form are also contemplated. Polymers suitable for particle formation include, but aren't limited to poly(d, l-lactic acid), poly(l-lactic acid), poly(d-lactic acid), poly (glycolic acid) and copolymers and mixtures of polylactate and polyglycolic. Other suitable polymers include methacrylate polymers, such as polybutyl methacrylate, ethylene vinyl alcohol (EVOH), .epsilon.-caprolactone, glycolide, ethylvinyl hydroxylated acetate (EVA), polyvinyl alcohol (PVA), polyethylene oxides (PEO), polyester amides, and co-polymers thereof and mixtures thereof. Typically, the composition is formulated to contain between 20-80 weight percent polymer and 20-80 weight percent rapamycin compound. An exemplary formulation contains between 20 and 60 weight percent of the rapamycin 40-O-cyclic hydrocarbon ester and 40 and 80 weight percent of a polylactate or polyglycolate polymer or a polylactate/polyglycolate copolymer or mixed polymer. The particles have typical sizes between about 0.1 micron to about 100 microns in diameter, preferably from about 0.5 microns to about 20 microns, and can be administered as liquid, paste, or gel suspension.

Drug-Coated Stent

In another general embodiment, the invention includes an endovascular stent coated with the drug alone or the drug formulated in a polymer coated, such as the drug-polymer formulations described above. Such stents are typically cylindrical, expandable metal-frame structures whose struts or filaments may be coated, on their outer surfaces, with a drug-eluting coating. When placed in a body lumen, a stent is expanded to press against the wall of the vessel and hold the stent in place, while drug is eluted from the stent against the wall of the vessel.

An exemplary coating contains equal amounts by weight of compound 1 and d,l PLA material, which may be formulated and applied to the stent outer surface according to well known methods. An example stent product is described in U.S. Pat. No. 7,214,759 where polymers containing polyesters and optional therapeutic agents are applied to implantable substrates, including stents. Coatings applied to the surface of stents may incorporate excipient materials along with the rapamycin 40 O-cyclic hydrocarbon esters which enhance the adhesion properties or elution profile of the drug, or impart other beneficial properties to the system. The coating may contain or be composed of micro or macroporous drug reservoirs. The coating may be comprised of the drug compound alone. Those familiar with the art are aware that these examples do not limit the scope of the invention.

IVB. Treating Restenosis: Compound Delivery from a Catheter Balloon

In another vascular application, rapamycin 40 O-cyclic hydrocarbon esters can be applied as a coating to the surface of the inflatable balloon portion of a percutaneous vascular angioplasty balloon catheter in a manner that when the balloon is placed adjacent to a vascular target lesion and then inflated the drug will separate from the balloon surface and transfer to the affected tissue. In this method of drug delivery the balloon distributes the drug homogenously along the arterial wall, whereas in drug-eluting stents the highest concentration is under the wire components of the stents. Whereas stents generally to permanently alter the vessel wall the drug coated balloon is removed after deployment, leaving only the remaining drug and coating. In U.S. Pat. No. 7,572,245 Herweck, et al. describe a means to deliver a therapeutic agent a vessel lumen by positioning a coated balloon within a target vessel and through inflation of the balloon atraumatically smearing the coating agent against the vascular lesion, thus transferring a portion through lipophilic absorptive action. In U.S. Pat. No. 7,750,041 Speck, et al. reveal an angiography catheter comprising a coating of paclitaxel and iopromide applied to the balloon portion of the catheter which is released to surrounding tissue upon balloon inflation.

Coatings applied to the surface of vascular balloons may incorporate excipient materials along with the rapamycin 40 O-cyclic hydrocarbon esters which enhance the adhesion properties or elution profile of the drug, or impart other beneficial properties to the system. The coating may contain or be composed of micro or macroporous drug reservoirs. The coating may be comprised of the drug compound alone.

IVC. Treating Ocular Disorders

Compounds in the subject invention may be used to treat ocular disorders. Rapamycin itself has been evaluated clinically for treatment of macular degeneration. In clinical trials subconjunctival injections of rapamycin in doses ranging from 220 micrograms to 880 micrograms to verify increased visual acuity in a 180 day timeframe. Rapamycin has also been applied systemically in conjunction with corticosteroids for treatment of non-infectious uveitis. The compounds of the subject can be utilized in valved or non-valved stents/shunts used for glaucoma drainage. In the present invention, the ocular disorders are treated by administering to a mammalian subject in need of treatment, a therapeutic amount of the rapamycin alkyl ester analog of the present invention.

Example I: Comparative Studies Between Sirolimus and Present Compounds in Rabbit Vitreous and Aqueous Humour In vitro studies were performed with New Zealand White rabbit vitreous humour (which is an acceptable predicate for human vitreous humour) and intravitreal administration of the rapamycin 40-O-cyclic hydrocarbon ester compounds of the present invention was varied by dosing and measured against sirolimus. The assay comparison between sirolimus and the compounds of the present invention (denoted as CRC) is further described at Table XI.

TABLE XI

Assay comparison of sirolimus (SIR) drug stability in rabbit vitreous and aqueous humour at 37° C. versus CRC

| Trial | Drug Dose (µg) | Drug Remaining 72 Hours (µg) | % Remaining | Drug Remaining 192 Hours (µg) | % Remaining |
|---|---|---|---|---|---|
| Rabbit Vitreous Humour | | | | | |
| SIR 1 | 48.4 | 4.0 | 8% | — | — |
| SIR 2 | 47.8 | — | — | 0.6 | 1% |
| CRC 1 | 52.2 | 28.0 | 54% | — | — |
| CRC 2 | 54.0 | — | — | 24.4 | 45% |
| CRC 3 | 261.8 | — | — | 235.2 | 90% |
| Rabbit Aqueous Humour | | | | | |
| SIR 1 | 45.2 | 0.0 | 0% | — | — |
| CRC 1 | 51.4 | 34.4 | 67% | — | — |

As evidenced in Table XI, there is a much larger amount of CRC available (versus SIR) present over time, in both the vitreous humour and aqueous humour. This is due to the fact that there is improved solubility of the rapamycin 40-O-cyclic hydrocarbon ester compounds of the present invention (embodied in CRC), when compared to sirolimus. This allows for a lower injection volume for a dose size equivalent to sirolimus or, if using the same injection volume of drug, a higher dosing can be delivered. This is particularly important when dealing with administration directly to the vitreous, as intravitreal treatment injection volume is necessarily restricted to less than 50 µl and is generally within the 20-25 ul range or preferably r less.

Figure 3:
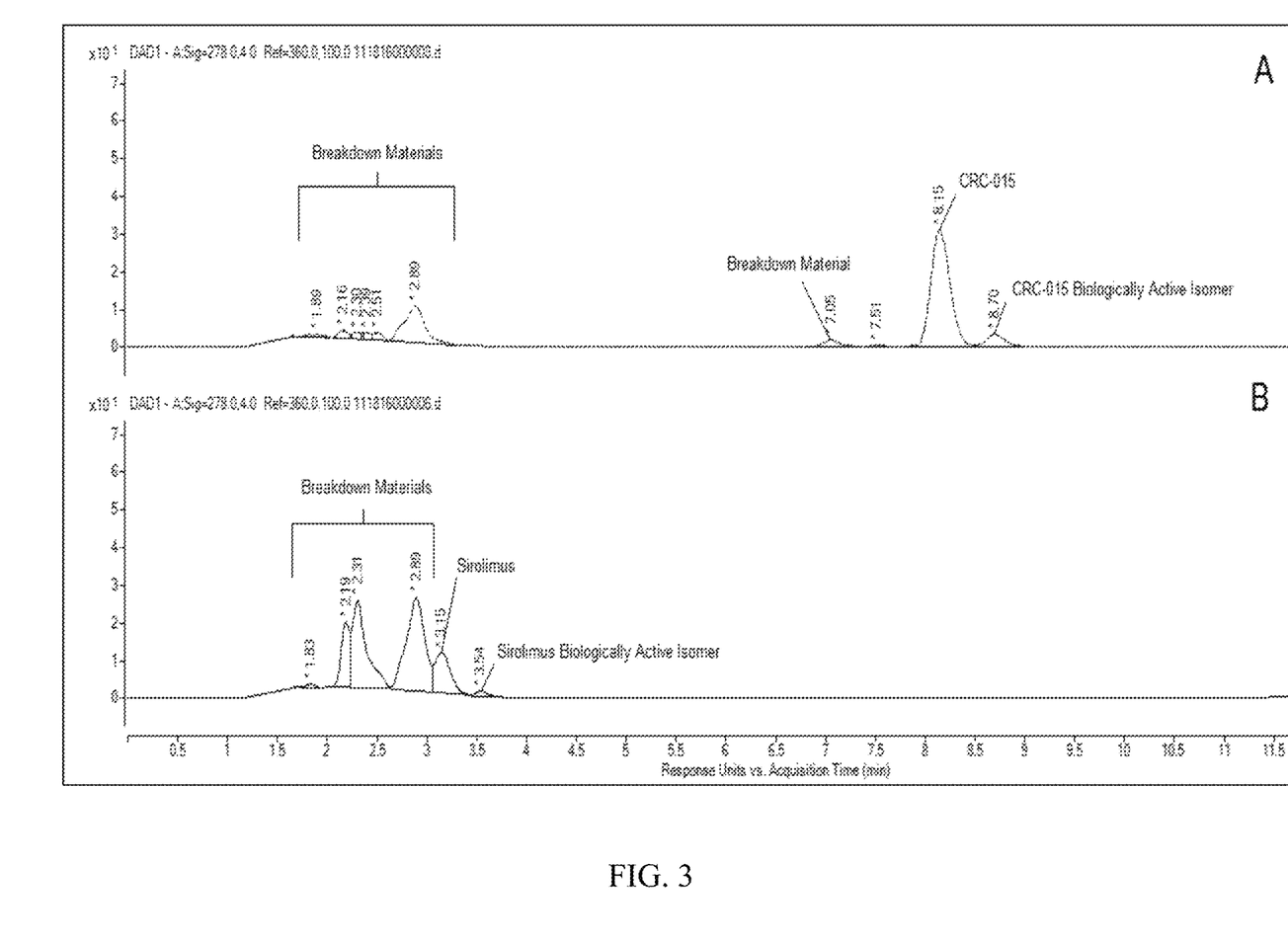
FIG. 3 shows a reverse phase HPLC comparison of drug breakdown materials after 72 hours incubation in rabbit vitreous humour at 37° C. (A) CRC; (B) sirolimus.

Additionally, CRC has much higher intravitreal chemical stability, which may allow for a longer interval between eye injections, as the drug levels are maintained for much longer time periods when compared to sirolimus. As shown at Tables XII and XIII, sirolimus is much more rapidly degraded over a shorter period of time when compared to CRC at both the vitreous humour and aqueous humour samples. This is further identified in reverse phase HPLC studies comparing the breakdown of SIR and CRC after 72 hours in rabbit vitreous humour (FIG. 3).

TABLE XII

Comparison of detected breakdown materials after incubation in rabbit vitreous humour at 37° C.

| | Rabbit Vitreous Humour (HPLC UV Area Percent) | | | |
|---|---|---|---|---|
| Time | Sirolimus | | CRC | |
| (hrs) | Degradants | Sirolimus | Degradants | CRC |
| 0 | 3% | 97% | 4% | 96% |
| 1 | 3% | 97% | 5% | 95% |
| 4 | 7% | 93% | 14% | 86% |
| 24 | 43% | 57% | 6% | 94% |
| 48 | 71% | 29% | 15% | 85% |
| 72 | 84% | 16% | 32% | 68% |

TABLE XIII

Comparison of detected breakdown materials after incubation in rabbit aqueous humour at 37° C.

| | Rabbit Aqueous Humour (HPLC UV Area Percent) | | | |
|---|---|---|---|---|
| Time | Sirolimus | | CRC | |
| (hrs) | Degradants | Sirolimus | Degradants | CRC |
| 0 | 2% | 98% | 1% | 99% |
| 1 | 4% | 96% | 2% | 98% |
| 4 | 18% | 82% | 14% | 86% |
| 24 | 86% | 14% | 11% | 89% |
| 48 | 96% | 4% | 16% | 84% |
| 72 | 100% | 0% | 22% | 78% |

U.S. Pat. No. 8,367,097 discloses liquid formulations containing rapamycin, polyethylene glycol and ethanol for the treatment of uveitis by intravitreal injection in humans. It has been shown that polyethylene glycol can cause severe ocular toxicity when injected intravitreally. (Patel et al., *J. OculPharmacol Ther* 32(2):97-101 (2016).

Another advantage of using the rapamycin 40-O-cyclic hydrocarbon ester compounds of the present invention over sirolimus is the ability to formulate CRC compounds in the absence of polyethylene glycol, resulting in a much cleaner chemistry, including only the active compound and ethanol (as opposed to sirolimus, which requires a solubilizing agent in the formulation such as PEG to allow for proper drug concentration contained in suitable injection volumes.). Similarly, as the CRC compounds are more lipophilic than sirolimus, there is a greater ability to penetrate into the target tissues, resulting in an increased potency.

One aspect of the invention is therefore directed to a pharmaceutical formulation comprising or consisting of CRC compounds as defined herein and ethanol. In a preferred embodiment of the formulation the concentration of CRC compounds as defined herein in ethanol is in the range of 1-wt-% to 60 wt-%, more preferred 10 to 57.5 wt-%, even more preferred in a range of 20- to 55 wt-% and most preferred in a range of 33.7 to 50.5 wt-%.

Also, the invention is directed to the use of such a pharmaceutical formulation for the treatment of ocular disorders such as uveitis or proliferative ophthalmic diseases as described herein. Also, the invention is directed to a dosage form comprising or consisting of a volume of the formulation as suggested herein.

IVD. Treating Cancers

Compounds in the subject invention are also useful in the treatment of cancer. Rapamycin itself is currently in clinical pancreatic cancer trials as well as skin cancer trials and breast cancer trials. The therapeutic effect of rapamycin and related compounds in cancer and malignant tumor treatment is likely caused by disruption of the biochemical pathways involved in the development of new blood vessels. Rapamycin when combined with cancer drug Carboplatin have also been found to potentially improve the efficiency of ovarian cancer treatment. Rapamycin has also been shown to inhibit the progression of dermal Kaposi's sarcoma. Other mTOR inhibitors, such as temsirolimus and everolimus are currently being tested for use in cancers such as glioblastoma multiforme and mantle cell lymphoma. In the present invention, a cancer is treated by administering to a mammalian subject in need of treatment, a therapeutic amount of the rapamycin 40-O-cyclic hydrocarbon ester analog of the present invention.

Example II: Cell Culture Inhibition Studies for CRC Compounds

In vitro mammalian cell culture inhibition studies are frequently used to predict biological in vivo responses. Various human cancer cell types were obtained from the American Type Culture Collection (ATCC) and cultured according to the vendor's recommendations. CRC was dissolved in dimethyl solfoxide (DMSO) and added to the culture medium at concentrations indicated. Controls consisted of DMSO only addition. Cell proliferation was measured using methylene blue staining by conventional methods.

Figure 4:
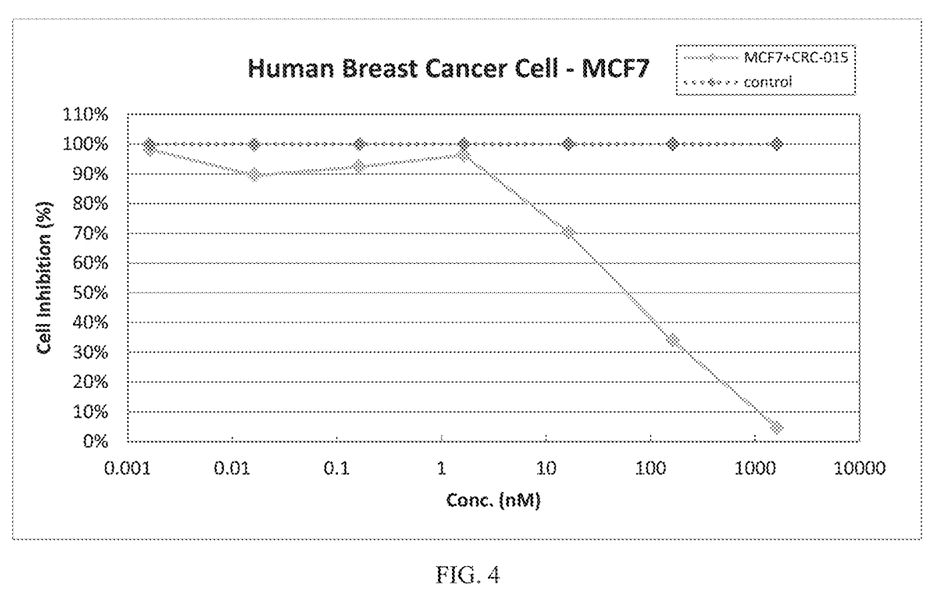
FIG. 4 shows results from a cell inhibition assay measuring the IC$_{50}$ of the rapamycin 40-O-cyclic hydrocarbon ester compounds of the present invention when applied to human breast cancer cell line MCF7.
Figure 5:
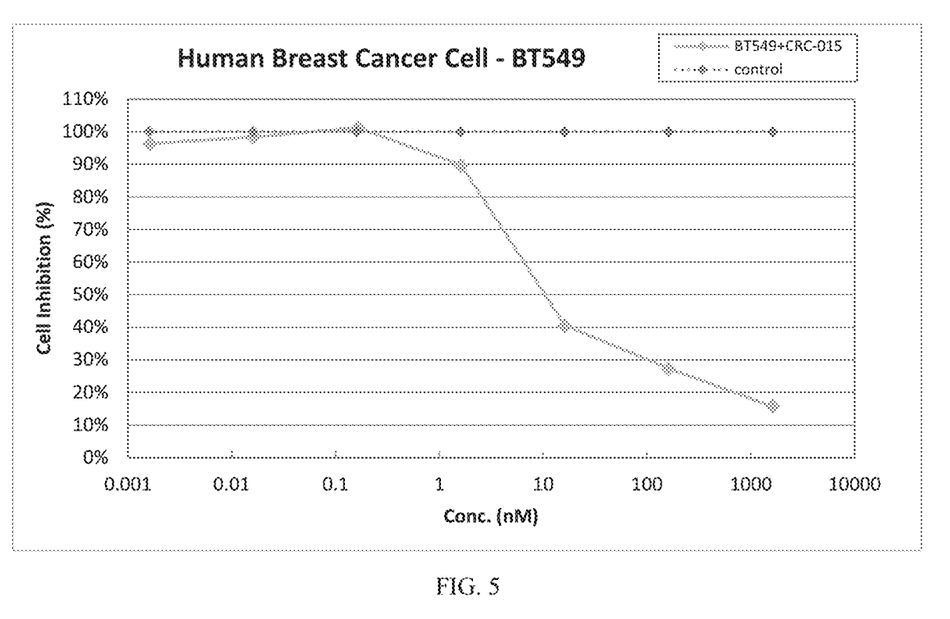
FIG. 5 shows results from a cell inhibition assay measuring the IC$_{50}$ of the rapamycin 40-O-cyclic hydrocarbon ester compounds of the present invention when applied to human breast cancer cell line BT549.
Figure 6:
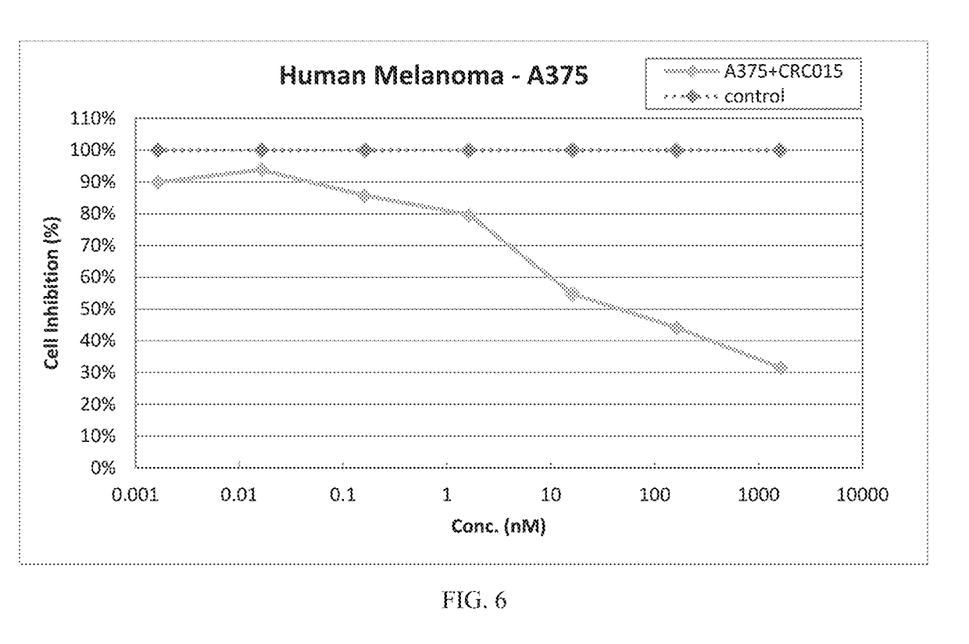
FIG. 6 shows results from a cell inhibition assay measuring the IC$_{50}$ of the rapamycin 40-O-cyclic hydrocarbon ester compounds of the present invention when applied to human melanoma cell line A375.
Figure 7:
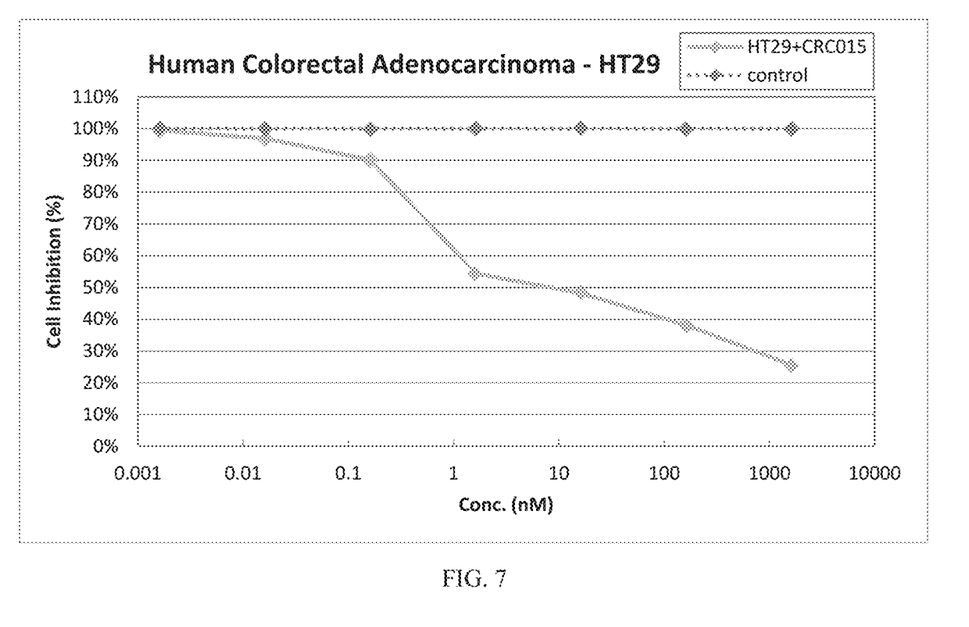
FIG. 7 shows results from a cell inhibition assay measuring the IC$_{50}$ of the rapamycin 40-O-cyclic hydrocarbon ester compounds of the present invention when applied to human colorectal adenocarcinoma cell line HT29.
Figure 8:
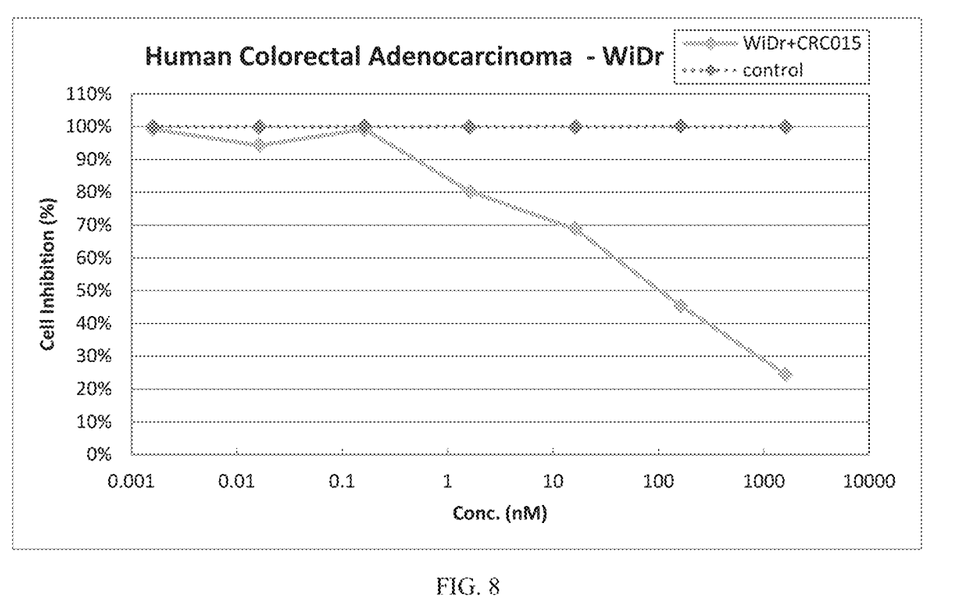
FIG. 8 shows results from a cell inhibition assay measuring the IC$_{50}$ of the rapamycin 40-O-cyclic hydrocarbon ester compounds of the present invention when applied to human colorectal adenocarcinoma cell line WiDr.
Figure 9:
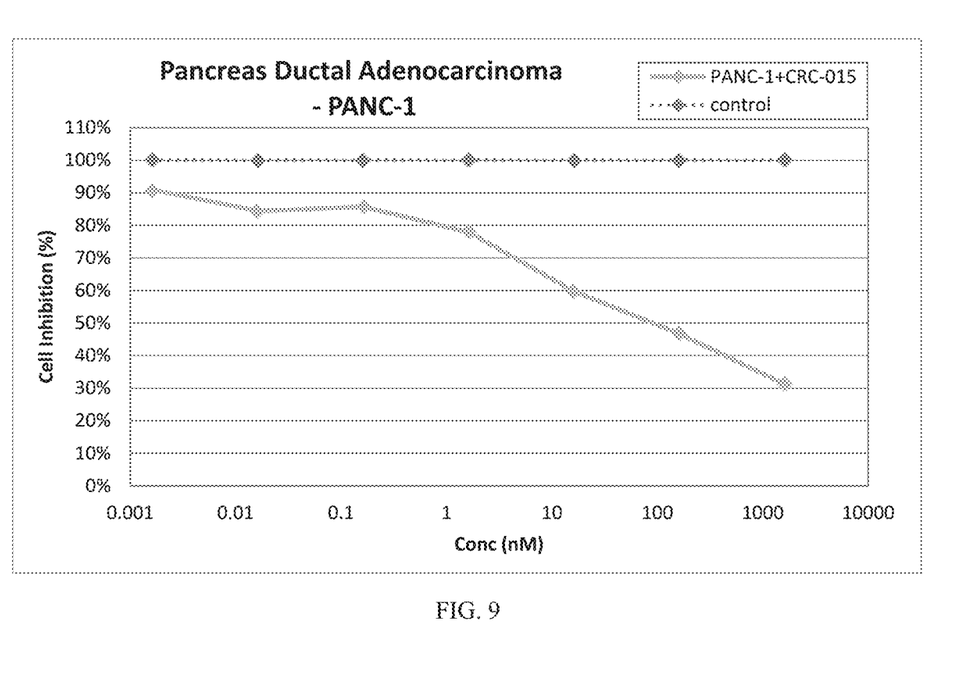
FIG. 9 shows results from a cell inhibition assay measuring the IC$_{50}$ of the rapamycin 40-O-cyclic hydrocarbon ester compounds of the present invention when applied to human pancreas ductal adenocarcinoma cell line PANC-1.
Figure 10:
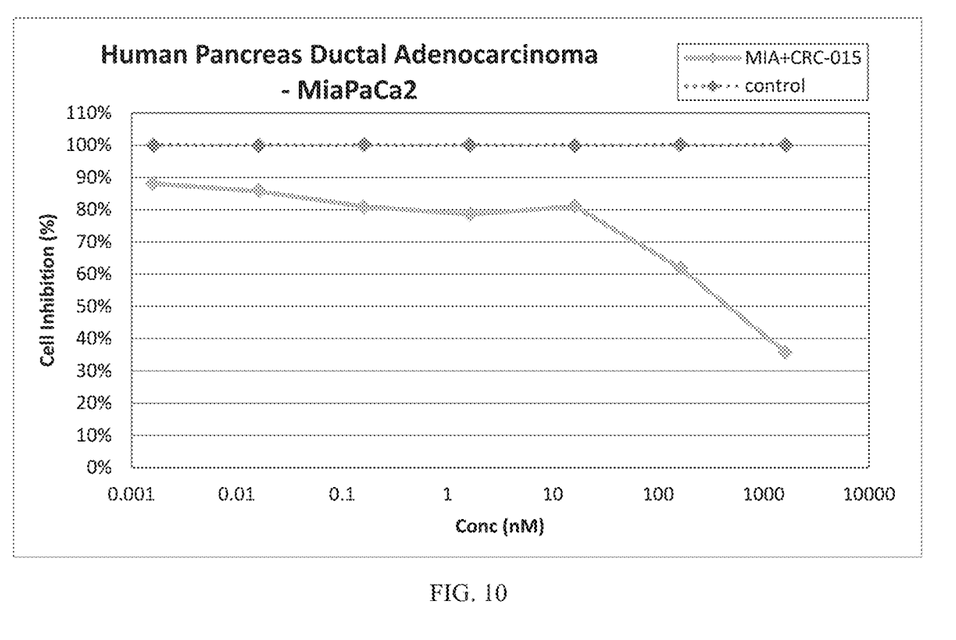
FIG. 10 shows results from a cell inhibition assay measuring the IC$_{50}$ of the rapamycin 40-O-cyclic hydrocarbon ester compounds of the present invention when applied to human pancreas ductal adenocarcinoma cell line MiaPaCa2.

The cell lines and the inhibition activity ($IC_{50}$) in the presence of CRC are described in the figures as follows: human breast cancer cell line MCF7; CRC $IC_{50}$=81 nM (FIG. 4), human breast cancer cell line BT549; CRC $IC_{50}$=8 nM (FIG. 5), human melanoma cell line A375; CRC $IC_{50}$=11 nM (FIG. 6), human colorectal adenocarcinoma cell line HT29; CRC $IC_{50}$=1 nM (FIG. 7), human colorectal adenocarcinoma cell line WiDr; CRC $IC_{50}$=107 nM (FIG. 8), pancreas ductal adenocarcinoma cell line PANC-1; CRC $IC_{50}$=15 nM (FIG. 9), human pancreas ductal adenocarcinoma cell line MiaPaCa2; CRC $IC_{50}$=252 nM (FIG. 10).

As evidenced in the data mentioned above, the inhibition of several human cancer cell types by the rapamycin 40-O-cyclic hydrocarbon ester compounds of the present invention at low nanomolar concentrations indicates utility of this material for oncology treatments. The present disclosure provides a method of treating cancer comprising administering an effective amount of the rapamycin 40-O-cyclic hydrocarbon ester compounds of the present invention at a nanomolar dosage range and a form of administration that delivers the compounds in a pharmaceutically acceptable form. Dosage forms well known in the art such as but not limited to pills, injections, creams, suppositories, depots, solutions, balloons and stents can be utilized to dose a mammal in need of treatment.

IVE. Prevention of Transplant Rejection

Rapamycin and its analogs can be used alone, or in conjunction with calcineurin inhibitors, such as tacrolimus to provide immunosuppression regimens. Transplant patients can be given oral medications which include rapamycin under the trade name Rapamune® or everolimus, a rapamycin analog under the trade name Certican® to reduce the incidence of tissue rejection. These therapies have the advantage of having lower toxicity toward kidneys. In the present invention, the subject is treated by administering a therapeutic amount of the rapamycin alkyl ester analog of the present invention.

Although the invention has been described with respect to particular embodiments and applications, it will be appreciated that various additional modification the applications may be made consistent with the scope of the claims.

We claim:

1. A pharmaceutical formulation comprising ethanol and 1-60 weight percent of a 40-O-cyclic hydrocarbon ester compound having the structure:

where R is C(O)—(CH$_2$)$_n$—X, n is 0, 1 or 2, X is a cyclic hydrocarbon having 3-8 carbons, optionally containing one or more unsaturated bonds, one or more linear-chain or cyclic carbon atoms may contain an OH or halide substitution, and the rapamycin parent structure may contain substitutions at non-40 positions.

2. The formulation of claim 1 consisting of ethanol and the rapamycin 40-O-cyclic hydrocarbon ester.

3. A dosage form comprising a volume of liquid of claim 1 or 2.

* * * * *